United States Patent
Ujita et al.

(10) Patent No.: US 9,815,768 B2
(45) Date of Patent: Nov. 14, 2017

(54) METHOD FOR PRODUCING 2-(HALOGENOMETHYL)-3-METHYLNITROBENZENE

(71) Applicant: SUMITOMO CHEMICAL COMPANY, LIMITED, Tokyo (JP)

(72) Inventors: Satoru Ujita, Takarazuka (JP); Takashi Miyamoto, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/112,617

(22) PCT Filed: Feb. 16, 2015

(86) PCT No.: PCT/JP2015/054900
§ 371 (c)(1),
(2) Date: Jul. 19, 2016

(87) PCT Pub. No.: WO2015/129592
PCT Pub. Date: Sep. 3, 2015

(65) Prior Publication Data
US 2016/0332956 A1   Nov. 17, 2016

(30) Foreign Application Priority Data
Feb. 28, 2014 (JP) ................. 2014-038518

(51) Int. Cl.
C07C 205/11 (2006.01)
C07C 201/12 (2006.01)
B01J 23/44 (2006.01)

(52) U.S. Cl.
CPC ............ *C07C 205/11* (2013.01); *B01J 23/44* (2013.01); *C07C 201/12* (2013.01)

(58) Field of Classification Search
CPC ....... C07C 201/12; C07C 205/11; B01J 23/44
See application file for complete search history.

(56) References Cited

U.S. PATENT DOCUMENTS

| | | | |
|---|---|---|---|
| 5,298,622 A | 3/1994 | Portoghese et al. | |
| 5,436,250 A | 7/1995 | Watjen et al. | |
| 2003/0144291 A1 | 7/2003 | Berg et al. | |
| 2006/0167301 A1 | 7/2006 | Yamada et al. | |
| 2007/0004719 A1 | 1/2007 | McKew et al. | |
| 2008/0004281 A1* | 1/2008 | Rao ..................... | A61K 31/495 514/249 |

FOREIGN PATENT DOCUMENTS

| | | |
|---|---|---|
| JP | 2-62875 A | 3/1990 |
| WO | WO 2013/162072 A1 | 10/2013 |

OTHER PUBLICATIONS

Yasui et al., Transition metal catalyzed reudction of organic halide (Journal of Organic Chemistry 1985, 50, 3283-3287).*
Cho et al., "Synthesis of Disulfide-Containing Aniline and Copolymerization with Aniline", Macromolecules 2001, 34, pp. 2751-2756.
International Search Report for PCT/JP2015/054900 dated May 26, 2015.
Makosza et al., "Specific Ortho Orientation in the Vicarious Substitution of Hydrogen in Aromatic Nitro Compounds with Carbanion of Chloromethyl Phenyl Sulfone[1]", Tetrahedron, vol. 40, No. 10, 1984, pp. 1863-1868.
International Preliminary Report on Patentability and English translation of the Written Opinion of the International Searching Authority (forms PCT/IB/373 and PCT/ISA/237), dated Sep. 6, 2016, for International Application No. PCT/JP2015/054900.
Chinese Office Action and Search Report for Chinese Application No. 20150009230.7, dated Jun. 9, 2017, with a partial English translation of the Office Action.
Yasui et al., "NAD(P)$^+$-NAD(P)H Models. 55. Transition Metal Catalyzed Reduction of Organic Halides: High Selectivity for Reductive Dehalogenation," J. Org. Chem., vol. 50, No. 18, 1985, pp. 3283-3287.

* cited by examiner

*Primary Examiner* — Jafar Parsa
(74) *Attorney, Agent, or Firm* — Birch, Stewart, Kolasch & Birch, LLP

(57) ABSTRACT

Position-1 halogen can be selectively reduced by reacting a compound represented by formula (3):

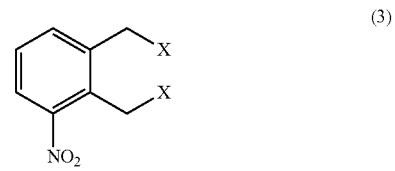

(3)

[wherein X represents a chlorine atom, a bromine atom, or an iodine atom]
with halogen in the presence of a heterogeneous transition metal catalyst to produce 2-(halogenomethyl)-1-methyl-3-nitrobenzene represented by formula (1):

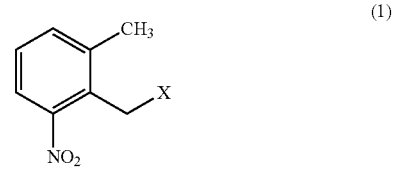

(1)

[wherein the symbol is as defined above].

9 Claims, No Drawings

METHOD FOR PRODUCING 2-(HALOGENOMETHYL)-3-METHYLNITROBENZENE

TECHNICAL FIELD

The present invention directs to a method for producing 2-(halogenomethyl)-3-methylnitrobenzene.

BACKGROUND ART

As described in WO 2013/162072, US 2007/004719, etc., 2-(halogenomethyl)-3-methylnitrobenzene is a compound useful as an intermediate in the production of pharmaceuticals and agrochemicals.

US 2006/167301 describes a dehalogenation reaction for reducing an aralkyl halide compound, and shows that 4'-methyl-2-cyanobiphenyl is obtained by reducing 4'-bromomethyl-2-cyanobiphenyl and 4'-dibromomethyl-2-cyanobiphenyl.

Meanwhile, the fact that a nitro compound is reduced to an amine compound in the presence of a palladium catalyst is well known, as described in "*Jikken Kagaku Koza* (Lectures on Experimental Science), 5th Ed., Vol. 14, Yuki-Kagobutsuno Gosei (Synthesis of Organic Compounds) II, Alcohol/Amine, p. 357.

SUMMARY OF THE INVENTION

The present invention provides a method for producing 2-(halogenomethyl)-3-methylnitrobenzene.

The present invention is a method for producing a compound represented by formula (1), including:
a step of allowing a compound represented by formula (3):

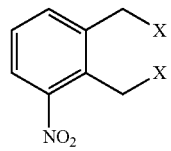

(3)

[wherein X represents a chlorine atom, a bromine atom, or an iodine atom]
to react with hydrogen in the presence of a heterogeneous transition metal catalyst, such as a heterogeneous palladium catalyst, thereby giving the compound represented by formula (1):

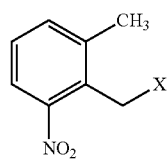

(1)

[wherein the symbol is as defined above].

In addition, the present invention is a method for producing a compound represented by formula (1), comprising:
step A of allowing a compound represented by formula (2):

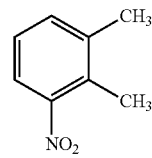

(2)

to react with one or more halogenating agents selected from the group consisting of chlorine, bromine, N-bromosuccinimide, sodium bromoisocyanurate, dibromoisocyanuric acid, 1,3-dibromo-5,5-dimethylhydantoin, iodine, and N-iodosuccinimide, thereby giving a compound represented by formula (3):

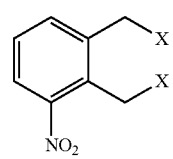

(3)

[wherein X represents a chlorine atom, a bromine atom, or an iodine atom]; and
step B of allowing the compound represented by formula (3) to react with hydrogen in the presence of a heterogeneous transition metal catalyst, such as a heterogeneous palladium catalyst, thereby giving the compound represented by formula (1):

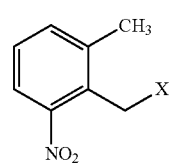

(1)

[wherein the symbol is as defined above].

MODE FOR CARRYING OUT THE INVENTION

Hereinafter, the present invention will be described in detail.

First, step A will be described.

A compound represented by formula (3) can be produced by allowing a compound represented by formula (2) to react with a halogenating agent.

The reaction is carried out in a solvent or in the absence of a solvent. Examples of the solvent include aromatic hydrocarbon solvents having an electron-withdrawing group on the aromatic ring, such as monochlorobenzene, monobromobenzene, nitrobenzene, and o-dichlorobenzene; halogenated hydrocarbon solvents such as dichloromethane, chloroform, dichloroethane, and carbon tetrachloride; ether solvents such as t-butyl methyl ether, tetrahydrofuran, dioxane, and diethyl ether; nitrile solvents such as benzonitrile, acetonitrile, and propionitrile; hydrocarbon solvents such as hexane, heptane, and cyclohexane; ester solvents such as methyl acetate, ethyl acetate, methyl propionate, and ethyl propionate; water; and mixed solvents thereof.

The amount of the solvent to be used is usually 0 to 100 times, preferably 0.5 to 70 times, relative to the weight of the compound represented by formula (3).

Examples of the halogenating agent include chlorine, bromine, N-bromosuccinimide, sodium bromoisocyanurate, dibromoisocyanuric acid, 1,3-dibromo-5,5-dimethylhydantoin, iodine, and N-iodosuccinimide. In terms of reaction efficiency, bromine is preferable.

The amount of the halogenating agent to be used is usually 0.5 to 10 times, preferably 1 to 4 times by mole, relative to the compound represented by formula (3).

In the case where bromine, N-bromosuccinimide, sodium bromoisocyanurate, dibromoisocyanuric acid, or 1,3-dibromo-5,5-dimethylhydantoin is used as a halogenating agent, it is preferable that the reaction is carried out in the presence of a radical initiator, and it is preferable that the radical initiator and the halogenating agent are simultaneously added dropwise to the reaction system.

Examples of the radical initiator include azobis compounds such as 2,2'-azobis(4-methoxy-2,4-dimethylvaleronitrile), 2,2'-azobis(2,4-dimethylvaleronitrile), 2,2'-azobis(isobutyronitrile) (hereinafter referred to as AIBN), 2,2'-azobis(2-methylbutyronitrile), and 1,1'-azobis(cyclohexane-1-carbonitrile); as well as peroxides such as benzoyl peroxide and di-t-butyl peroxide. AIBN, benzoyl peroxide, 2,2'-azobis(2-methylbutyronitrile), and 1,1'-azobis(cyclohexane-1-carbonitrile) are preferable, and, in terms of availability, AIBN and benzoyl peroxide are still more preferable.

The amount of the radical initiator to be used is usually 0.1 to 10 mol %, preferably 1 to 6 mol %, relative to the compound represented by formula (3).

The radical initiator may also be dissolved in the above solvent before addition.

In the case where chlorine is used as a halogenating agent, the reaction is carried out under UV light irradiation. The light source of UV light only needs to be light with a wavelength of 180 nm to 400 nm, and a light source of 250 nm to 350 nm is preferable. As the light source, a high-pressure mercury lamp, a low-pressure mercury lamp, or the like is used.

In the case where chlorine, bromine, or iodine is used as a halogenating agent, hydrogen halide is produced as a by-product of the reaction. However, the by-product hydrogen halide can be converted into chlorine, bromine, or iodine by an oxidizing agent and reused as a halogenating agent.

Examples of the oxidizing agent include hypohalites such as sodium hypochlorite, sodium hypobromite, sodium hypoiodite, potassium hypochlorite, potassium hypobromite, and potassium hypoiodite; halites such as sodium chlorite, sodium bromite, sodium iodite, potassium chlorite, potassium bromite, and potassium iodite; halates such as sodium chlorate, sodium bromate, sodium iodate, potassium chlorate, potassium bromate, and potassium iodate; perhalates such as sodium perchlorate, sodium perbromate, sodium periodate, potassium perchlorate, potassium perbromate, and potassium periodate; and hydrogen peroxide. Halites and halates are preferable, and sodium chlorite, potassium chlorite, sodium chlorate, potassium chlorate, sodium bromate, and potassium bromate are still more preferable.

The amount of the oxidizing agent to be used is usually 0.1 to 5 times, preferably 0.2 to 0.8 times by mole, relative to chlorine, bromine, or iodine to serve as a halogenating agent.

The oxidizing agent may be used in the form of an aqueous solution.

The reaction temperature varies depending on the halogenating agent or the radical initiator, but is usually 0 to 120° C., preferably 25 to 110° C.

The reaction time is usually 2 to 24 hours.

After the completion of the reaction, the residual halogenating agent may be removed by a reduction treatment. The reduction treatment can be performed using an aqueous solution of sodium hydrogensulfite, potassium hydrogensulfite, sodium sulfite, potassium sulfite, or the like.

As necessary, the obtained compound represented by formula (3) may be subjected to washing with water, concentration, crystallization, filtration, or the like and then allowed to react with hydrogen in step B, or may be further purified by recrystallization, distillation, column chromatography, or the like and then allowed to react with hydrogen in step B.

Next, step B will be described.

A compound represented by formula (1) can be produced by allowing a compound represented by formula (3) to react with hydrogen in the presence of a heterogeneous transition metal catalyst.

The reaction is carried out in a solvent or in the absence of a solvent. Examples of the solvent include aromatic hydrocarbon solvents such as toluene, xylene, and ethylbenzene; ether solvents such as t-butyl methyl ether, tetrahydrofuran, dioxane, and diethyl ether; hydrocarbon solvents such as hexane, heptane, and cyclohexane; ester solvents such as methyl acetate, ethyl acetate, methyl propionate, and ethyl propionate; alcohol solvents such as methanol, ethanol, propanol, isopropyl alcohol, and butanol; water; and mixed solvents thereof.

The amount of the solvent to be used is usually 0 to 100 times, preferably 0.5 to 20 times by weight, relative to the compound represented by formula (3).

Examples of the heterogeneous transition metal catalyst include heterogeneous palladium catalysts such as palladium/carbon, palladium/silica, palladium/alumina, palladium/barium sulfate; heterogeneous platinum catalysts such as platinum/carbon, platinum/silica, and platinum/alumina; heterogeneous ruthenium catalysts such as ruthenium/carbon, ruthenium/silica, and ruthenium/alumina; heterogeneous rhodium catalysts such as rhodium/carbon, rhodium/silica, and rhodium/alumina; heterogeneous iridium catalysts such as iridium/carbon; heterogeneous osmium catalysts such as osmium/carbon; heterogeneous nickel catalysts such as nickel/diatomaceous earth catalysts and Raney nickel; and heterogeneous cobalt catalysts such as Raney cobalt catalysts. Heterogeneous platinum group catalysts including palladium, platinum, ruthenium, rhodium, iridium, and osmium, which are platinum-group elements, are preferable. As an industrial production method, heterogeneous palladium catalysts are still more preferable, and palladium/carbon is most preferable. The metal content of the heterogeneous transition metal catalyst is usually 1 to 20 wt %, preferably 5 to 10 wt %.

The amount of the heterogeneous transition metal catalyst to be used is, as a metal contained in the heterogeneous transition metal catalyst, usually 0.01 to 2 mol %, preferably 0.05 to 1 mol %, relative to the compound represented by formula (3).

In the case where the compound represented by formula (3) is allowed to react with hydrogen in a hydrogen atmosphere, the hydrogen partial pressure is usually 0.01 MPa to 1 MPa, preferably 0.05 to 0.5 MPa.

A neutralizer may also be added in order to neutralize hydrogen halide produced as a by-product of the reaction. Examples of the neutralizer include alkaline earth metal hydroxides such as magnesium hydroxide and calcium hydroxide; alkaline earth metal carbonates such as magnesium carbonate and calcium carbonate; alkaline earth metal oxides such as magnesium oxide and calcium oxide; alkali metal hydroxides such as lithium hydroxide, sodium hydroxide, and potassium hydroxide; alkali metal carbonates such as lithium carbonate, sodium carbonate, and potassium carbonate; and alkali metal hydrogen carbonates such as lithium hydrogen carbonate, sodium hydrogen carbonate, and potassium hydrogen carbonate.

The amount of the neutralizer to be used varies depending on the amount of hydrogen halide produced as a by-product, but is usually 0.1 to 10 times, preferably 0.5 to 3 times by mole, relative to the compound represented by formula (3).

The reaction temperature is usually 0° C. or more, preferably 0 to 40° C., and particularly preferably 0 to 25° C. It is preferable that palladium/carbon is used as a heterogeneous palladium catalyst, and the reaction is carried out at 0 to 25° C.

The reaction time is usually 1 to 48 hours.

After the completion of the reaction, for example, the catalyst is removed by filtration, and the filtrate is concentrated, whereby a compound represented by formula (1) can be obtained. The compound may be further isolated or purified by recrystallization, distillation, chromatography, or the like.

EXAMPLES

Hereinafter, the present invention will be described in detail with reference to examples. However, the present invention is not limited only to these examples.

The UV light used in the examples was performed using the following device.

Light source: High-pressure UV lamp (100 W) UM-102 (Ushio Inc.)

High-pressure lamp lighting device: UM-103 B-B (Ushio Inc.)

The GC analysis conditions used in the examples are as follows.

Column: DB-5, 30 m in length, 0.53 mm in inner diameter, 1.50 μm in thickness (manufactured by Agilent Technologies, Agilent J&W GC Column)

Detection method: FID

Linear velocity: 60 cm/sec (helium)

Column temperature: 120° C. (5 min), −200° C. (2.5° C./min), −300° C. (10 min)

Injector temperature: 250° C.

Detector temperature: 300° C.

Example 1

A mixture of 1.50 g (0.0099 mol) of 2,3-dimethylnitrobenzene, 15.0 g of monochlorobenzene, 0.14 g (0.0006 mol) of benzoyl peroxide, and 2.63 g (0.015 mol) of N-bromosuccinimide was stirred at 100° C. for 3 hours. The mixture was sampled and subjected to GC analysis. As a result, the area percentages were as follows.
2-(Bromomethyl)-3-methylnitrobenzene: 20.2%
3-(Bromomethyl)-2-methylnitrobenzene: 34.7%
2,3-Bis(bromomethyl) nitrobenzene: 34.4%
2-(Bromomethyl)-3-(dibromomethyl) nitrobenzene: 1.7%

Example 2

To 10.0 g of monochlorobenzene, 5.0 g (0.033 mol) of 2,3-dimethylnitrobenzene and 10.4 g (0.0364 mol) of 1,3-dibromo-5,5-dimethylhydantoin were added and heated to 75 to 80° C. A solution prepared by dissolving 0.19 g (0.0012 mol) of AIBN in 5.0 g of monochlorobenzene was added dropwise at 70 to 80° C. over 1 hour and stirred at the same temperature for 2 hours. The mixture was cooled to 25° C., then 20 g of water was added, and the layers were separated. The obtained organic layer was concentrated at reduced pressure to give 10.25 g of a concentrate. As a result of GC analysis of the concentrate, the area percentages were as follows.
2-(Bromomethyl)-3-methylnitrobenzene: 5.5%
3-(Bromomethyl)-2-methylnitrobenzene: 11.1%
2,3-Bis(bromomethyl) nitrobenzene: 60.6%
2-(Bromomethyl)-3-(dibromomethyl) nitrobenzene: 10.4%

Example 3

A mixture of 1.00 g (0.0066 mol) of 2,3-dimethylnitrobenzene, 10.0 g of monochlorobenzene, and 0.08 g (0.0003 mol) of benzoyl peroxide was heated to 85° C., and 3.10 g (0.019 mol) of bromine was added dropwise over 2 hours, followed by stirring at the same temperature for 6 hours. Next, 3.17 g (0.020 mol) of bromine was added dropwise and further stirred for 9 hours. The reaction mixture was sampled and subjected to GC analysis. As a result, the area percentages were as follows.
2,3-Dimethylnitrobenzene: 28.1%
2-(Bromomethyl)-3-methylnitrobenzene: 23.1%
3-(Bromomethyl)-2-methylnitrobenzene: 35.5%
2,3-Bis(bromomethyl)nitrobenzene: 4.4%

Example 4

A mixture of 1.00 g (0.0066 mol) of 2,3-dimethylnitrobenzene, 10.1 g of nitrobenzene, and 0.09 g (0.0004 mol) of benzoyl peroxide was heated to 85° C., and 3.10 g (0.019 mol) of bromine was added dropwise over 2 hours, followed by stirring at the same temperature for 6 hours. Next, 3.17 g (0.020 mol) of bromine was added dropwise and further stirred for 9 hours. The reaction mixture was sampled and subjected to GC analysis. As a result, the area percentages were as follows.
2,3-Dimethylnitrobenzene: 32.3%
2-(Bromomethyl)-3-methylnitrobenzene: 24.1%
3-(Bromomethyl)-2-methylnitrobenzene: 36.1%
2,3-Bis(bromomethyl)nitrobenzene: 3.8%

Example 5

To a mixture of 2.00 g (0.013 mol) of 2,3-dimethylnitrobenzene and 0.16 g (0.00066 mol) of benzoyl peroxide, 3.17 g (0.020 mol) of bromine was added dropwise over 20 minutes, and followed by stirring at 60° C. for 2 hours and then at 110° C. for 6 hours. The reaction mixture was sampled and subjected to GC analysis. As a result, the area percentage of 2,3-bis(bromomethyl) nitrobenzene was as follows.
2,3-Dimethylnitrobenzene: 26.7%
2-(Bromomethyl)-3-methylnitrobenzene: 22.9%
3-(Bromomethyl)-2-methylnitrobenzene: 33.7%
2,3-Bis(bromomethyl) nitrobenzene: 6.6%

Next, 0.16 g (0.0007 mol) of benzoyl peroxide was added, and then 1.50 g (0.009 mol) of bromine was added dropwise over 1 hour, followed by stirring at 110° C. for 7 hours. The reaction mixture was sampled and subjected to GC analysis. As a result, the area percentages were as follows.
2,3-Dimethylnitrobenzene: 1.0%
2-(Bromomethyl)-3-methylnitrobenzene: 21.5%
3-(Bromomethyl)-2-methylnitrobenzene: 33.1%
2,3-Bis(bromomethyl) nitrobenzene: 26.7%
2-(Bromomethyl)-3-(dibromomethyl) nitrobenzene: 0.8%

Example 6

To 200.0 g of monochlorobenzene, 100.0 g (0.661 mol) of 2,3-dimethylnitrobenzene, 17.4 g of water and 14.97 g (0.099 mol) of sodium bromate were added and heated to 75 to 80° C. A solution prepared by dissolving 3.80 g (0.023 mol) of AIBN in 100.0 g of monochlorobenzene and 58.1 g (0.363 mol) of bromine were simultaneously added dropwise at 70 to 80° C. over 5 hours and stirred at the same temperature for 1 hour. The mixture was cooled to 25° C., then 200 g of water was added, and the layers were separated. The organic layer was concentrated at reduced pressure to give 153.20 g of a concentrate. As a result of GC analysis of the concentrate, the area percentages were as follows.
2,3-Dimethylnitrobenzene: 14.5%
2-(Bromomethyl)-3-methylnitrobenzene: 29.2%
3-(Bromomethyl)-2-methylnitrobenzene: 44.5%
2,3-Bis(bromomethyl)nitrobenzene: 9.7%
2-(Bromomethyl)-3-(dibromomethyl)nitrobenzene: Traces Example 7

To 10.0 g of monochlorobenzene, 5.0 g (0.033 mol) of 2,3-dimethylnitrobenzene, 3.0 g of water and 1.50 g (0.0099 mol) of sodium bromate were added and heated to 75 to 80° C. A solution prepared by dissolving 0.19 g (0.0012 mol) of AIBN in 5.0 g of monochlorobenzene and 5.81 g (0.036 mol) of bromine were simultaneously added dropwise at 70 to 80° C. over 1 hour and stirred at the same temperature for 2 hours. The mixture was cooled to 25° C., then 20 g of water was added, and the layers were separated. The obtained organic layer was concentrated at reduced pressure to give 10.38 g of a concentrate. As a result of GC analysis of the concentrate, the area percentages were as follows.
2-(Bromomethyl)-3-methylnitrobenzene: 9.7%
3-(Bromomethyl)-2-methylnitrobenzene: 17.7%
2,3-Bis(bromomethyl) nitrobenzene: 56.3%
2-(Bromomethyl)-3-(dibromomethyl) nitrobenzene: 5.2%

Example 8

To 10.0 g of monochlorobenzene, 5.0 g (0.033 mol) of 2,3-dimethylnitrobenzene, 3.0 g of water and 1.41 g (0.0132 mol) of sodium chlorate were added and heated to 75 to 80° C. A solution prepared by dissolving 0.19 g (0.0012 mol) of AIBN in 5.0 g of monochlorobenzene and 6.34 g (0.040 mol) of bromine were simultaneously added dropwise at 70 to 80° C. over 1 hour and stirred at the same temperature for 2 hours. The mixture was cooled to 25° C., then 20 g of water was added, and the layers were separated. The obtained organic layer was concentrated at reduced pressure to give 10.21 g of a concentrate. As a result of GC analysis of the concentrate, the area percentages were as follows.
2-(Bromomethyl)-3-methylnitrobenzene: 14.3%
3-(Bromomethyl)-2-methylnitrobenzene: 24.1%
2,3-Bis(bromomethyl) nitrobenzene: 48.4%
2-(Bromomethyl)-3-(dibromomethyl) nitrobenzene: 3.7%

Example 9

In a reaction vessel, 1.00 g (0.0066 mol) of 2,3-dimethylnitrobenzene and 50.0 g of monochlorobenzene were placed and followed by replacement with nitrogen. Subsequently, while bubbling chlorine gas at 25° C., the reaction vessel was irradiated with UV light for 10 hours using a 100 W high-pressure UV lamp. The reaction mixture was sampled and subjected to GC analysis. As a result, the area percentages were as follows.
2,3-Dimethylnitrobenzene: 27.6%
2-(chloromethyl)-3-methylnitrobenzene: 9.8%
3-(chloromethyl)-2-methylnitrobenzene: 21.2%
2,3-Bis(chloromethyl)nitrobenzene: 2.7%
2-(chloromethyl)-3-(dichloromethyl)nitrobenzene: Traces In the analysis, 2,3-bis(chloromethyl)nitrobenzene and 2-(chloromethyl)-3-(dichloromethyl)nitrobenzene were synthesized by nitrating 1,2-bis(chloromethyl)benzene and 1-(chloromethyl)-2-(dichloromethyl)benzene, respectively, and the agreement of the elution positions on the GC chromatogram was confirmed.

2,3-Bis(chloromethyl)nitrobenzene

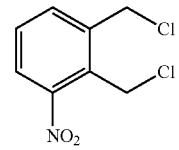

(6)

$^1$H-NMR (400 MHz, CDCl$_3$) δ: 4.81 (2H, s), 4.96 (2H, s), 7.53 (1H, t, J=7.93 Hz), 7.68 (1H, dd, J=7.70 Hz, 1.36 Hz), 7.90 (1H, dd, J=8.15 Hz, 1.36 Hz)

2-(chloromethyl)-3-(dichloromethyl)nitrobenzene

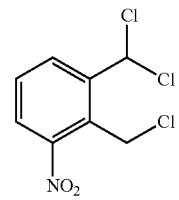

(7)

$^1$H-NMR (400 MHz, CDCl$_3$) δ: 4.89 (2H, s), 7.19 (1H, s), 7.64 (1H, t, J=8.0 Hz), 7.92 (1H, dd, J=8.0 Hz, 1.2 Hz), 8.22 (1H, dd, J=7.9 Hz, 1.4 Hz)

Example 10

In a reaction vessel, 1.00 g (0.0066 mol) of 2,3-dimethylnitrobenzene and 61.0 g of chloroform were placed and followed by replacement with nitrogen. Subsequently, while bubbling chlorine gas at 25° C., the reaction vessel was irradiated with UV light for 7.5 hours using a 100 W high-pressure UV lamp. The reaction mixture was sampled and subjected to GC analysis. As a result, the area percentages were as follows.

2,3-Dimethylnitrobenzene: 15.5%
2-(chloromethyl)-3-methylnitrobenzene: 11.1%
3-(chloromethyl)-2-methylnitrobenzene: 15.0%
2,3-Bis(chloromethyl)nitrobenzene: 4.5%
2-(chloromethyl)-3-(dichloromethyl)nitrobenzene: Traces

Example 11

In a reaction vessel, 1.00 g (0.0066 mol) of 2,3-dimethylnitrobenzene and 61.3 g of chloroform were placed and followed by replacement with nitrogen. Subsequently, 3.10 g (0.019 mol) of bromine was added dropwise at 25° C. over 30 minutes, and the reaction vessel was irradiated with UV light for 9 hours using a 100 W high-pressure UV lamp. Subsequently, 2.95 g (0.018 mol) of bromine was added dropwise at 35° C. over 1 hour, then stirred for 4 hours, and further irradiated with UV light at 40° C. for 4 hours. The reaction mixture was sampled and subjected to GC analysis. As a result, the area percentages were as follows.
2,3-Dimethylnitrobenzene: 71.7%
2-(Bromomethyl)-3-methylnitrobenzene: 13.7%
3-(Bromomethyl)-2-methylnitrobenzene: 8.1%
2,3-Bis(bromomethyl) nitrobenzene: 0.8%
2-(Bromomethyl)-3-(dibromomethyl) nitrobenzene: 0.2%

Example 12

To 0.77 g of a mixture containing 2,3-bis(bromomethyl) nitrobenzene in a GC area percentage of 96.1%, 28.8 mg of 5% Pd/C (53.5% wet product), 68.8 mg of magnesium oxide, 0.07 g of water and 9.7 g of methanol were added and followed by stirring in a hydrogen gas atmosphere at 0 to 10° C. for 3.5 hours. The reaction mixture was sampled and subjected to GC analysis. As a result, the area percentage of 2-(bromomethyl)-3-methylnitrobenzene was 55.9%.

Example 13

To 0.75 g of a mixture containing 2,3-bis(bromomethyl) nitrobenzene in a GC area percentage of 96.1%, 27.8 mg of 5% Pd/C (53.5% wet product), 68.3 mg of magnesium oxide, 45 mg of water and 9.4 g of 2-propanol were added and followed by stirring in a hydrogen gas atmosphere at 0 to 10° C. for 6 hours and then at 20° C. for 2 hours. The reaction mixture was sampled and subjected to GC analysis. As a result, the area percentage of 2-(bromomethyl)-3-methylnitrobenzene was 62.3%.

Example 14

To 1.00 g of a mixture containing 2,3-bis(bromomethyl) nitrobenzene in a GC area percentage of 54.1%, 41.6 mg of 5% Pd/C (58.2% wet product), 64.8 mg of magnesium oxide, 48 mg of water and 10.1 g of methanol were added and followed by stirring in a hydrogen gas atmosphere at room temperature for 16.5 hours. Subsequently, after replacement with nitrogen gas, the reaction mixture was filtered, and the resulting filtrate was concentrated at reduced pressure. Toluene and water were added to the residue, and the layers were separated. The obtained toluene solution was concentrated at reduced pressure to give 0.23 g of a concentrate. As a result of GC analysis of the concentrate, the area percentage of 2-(bromomethyl)-3-methylnitrobenzene was 52.4%.

Example 15

To 5.05 g of monochlorobenzene, 10.05 g (0.0662 mol) of 2,3-dimethylnitrobenzene, 6.00 g of water and 2.99 g (0.0198 mol) of sodium bromate were added and heated to 75 to 80° C. A solution prepared by dissolving 0.08 g (0.00049 mol) of AIBN in 1.0 g of monochlorobenzene was added and stirred for 30 minutes, and subsequently, a solution prepared by dissolving 0.62 g (0.0038 mol) of AIBN in 4.0 g of monochlorobenzene and 11.63 g (0.0728 mol) of bromine were simultaneously added dropwise at 70 to 80° C. and stirred at the same temperature for 7 hours. The mixture was cooled to 25° C., then an aqueous sodium sulfite solution and monochlorobenzene were added, and the layers were separated. The organic layer was washed with a saturated sodium bicarbonate solution and saturated saline and concentrated at reduced pressure to give 21.85 g of a concentrate. As a result of GC analysis of the concentrate, the area percentage of 2,3-bis(bromomethyl)nitrobenzene was 62.3%.

To 10.04 g of the reaction mixture obtained in the above step, 100.06 g of methanol was added and followed by cooling to 5° C. 0.40 g of 5% Pd/C (58.2% wet product) was added and stirred in a hydrogen gas atmosphere at 5° C. for 9.5 hours. After replacement with nitrogen gas, the reaction mixture was filtered to give 134.01 g of a methanol solution. As a result of analyzing the obtained methanol solution by GC internal standard method, the content of 2-(bromomethyl)-3-methylnitrobenzene was 1.34 g. (Total yield from 2,3-dimethylnitrobenzene: 47.2%).

Example 16

To 3.81 g of monochlorobenzene, 7.50 g (0.0496 mol) of 2,3-dimethylnitrobenzene, 4.55 g of water and 2.31 g (0.0149 mol) of sodium bromate were added and heated to 75 to 80° C. A solution prepared by dissolving 0.07 g (0.00043 mol) of AIBN in 0.77 g of monochlorobenzene was added and stirred for 30 minutes, and subsequently, a solution prepared by dissolving 0.46 g (0.0028 mol) of AIBN in 3.0 g of monochlorobenzene and 8.72 g (0.0546 mol) of bromine were simultaneously added dropwise at 70 to 80° C. over 8 hours and stirred at the same temperature for 13 hours. Further, 2.38 g (0.0149 mol) of bromine and 0.19 g (0.0011 mol) of AIBN were added and stirred at 80° C. for 4 hours, followed by cooling to 25° C., then monochlorobenzene and water were added, and the layers were separated. The organic layer was washed with saturated saline and concentrated at reduced pressure to give 15.94 g of a concentrate. As a result of GC analysis of the concentrate, the area percentage of 2,3-bis(bromomethyl)nitrobenzene was 56.7%.

To 15.94 g of the reaction mixture obtained in the above step, 159.6 g of methanol was added and followed by cooling to 5° C. 0.623 g of 5% Pd/C (58.2% wet product) was added and stirred in a hydrogen gas atmosphere at 5° C. for 6 hours. After replacement with nitrogen gas, the reaction mixture was filtered to give 220.26 g of a methanol solution. As a result of analyzing the obtained methanol solution by GC internal standard method, the content of 2-(bromomethyl)-3-methylnitrobenzene was 4.43 g. (Total yield from 2,3-dimethylnitrobenzene: 38.8%).

Example 17

To 3.02 g (0.0098 mol) of 2,3-bis(bromomethyl)nitrobenzene, 30.05 g of methanol was added and followed by cooling to 5° C. 61.9 mg of 5% Pd/C (58.2% wet product) was added and stirred in a hydrogen gas atmosphere at 5° C. for 4 hours. After replacement with nitrogen gas, the reaction mixture was filtered to give 52.21 g of a methanol solution. As a result of analyzing the obtained methanol solution by GC internal standard method, the content of 2-(bromomethyl)-3-methylnitrobenzene was 1.35 g. (Yield: 59.9%).

INDUSTRIAL APPLICABILITY

According to the present invention, 2-(halogenomethyl)-1-methyl-3-nitrobenzene can be produced efficiently on an industrial scale.

The invention claimed is:

1. A method for producing a compound of formula (1), comprising a step of allowing a compound of formula (3):

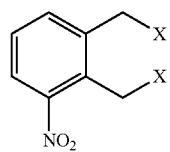
(3)

wherein X represents a chlorine atom, a bromine atom, or an iodine atom to react with hydrogen in the presence of a heterogeneous transition metal catalyst, thereby giving the compound of formula (1):

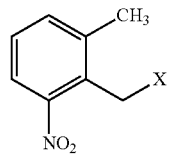
(1)

wherein X is as defined above.

2. The method according to claim 1, wherein the heterogeneous transition metal catalyst is a heterogeneous palladium catalyst.

3. The method according to claim 1, wherein the compound of formula (3) is allowed to react with hydrogen at a temperature of 0 to 40° C.

4. The method according to claim 1, wherein the heterogeneous transition metal catalyst is palladium/carbon, and the compound of formula (3) is allowed to react with hydrogen at a temperature of 0 to 25° C.

5. A method for producing a compound of formula (1), comprising:

a step of allowing a compound of formula (2):

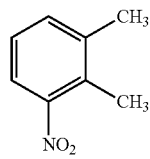
(2)

to react with one or more halogenating agents selected from the group consisting of chlorine, bromine, N-bromosuccinimide, sodium bromoisocyanurate, dibromoisocyanuric acid, 1,3-dibromo-5,5-dimethylhydantoin, iodine, and N-iodosuccinimide, thereby giving a compound of formula (3):

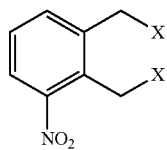
(3)

wherein X represents a chlorine atom, a bromine atom, or an iodine atom; and a step of allowing the compound of formula (3) to react with hydrogen in the presence of a heterogeneous transition metal catalyst, thereby giving the compound of formula (1):

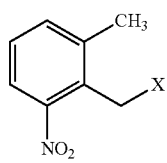
(1)

wherein X is as defined above.

6. The method according to claim 5, wherein the heterogeneous transition metal catalyst is a heterogeneous palladium catalyst.

7. The method according to claim 5, wherein the compound of formula (3) is allowed to react with hydrogen at a temperature of 0 to 40° C.

8. The method according to claim 5, wherein the heterogeneous transition metal is palladium/carbon, and the compound of formula (3) is allowed to react with hydrogen at a temperature of 0 to 25° C.

9. The method according to claim 5, wherein the compound of formula (2) is allowed to react with the halogenating agent in the presence of a radical initiator.

* * * * *